(12) United States Patent
Baker et al.

(10) Patent No.: US 9,962,536 B2
(45) Date of Patent: May 8, 2018

(54) DRAPED MICRONEEDLE ARRAY

(71) Applicant: KIMBERLY-CLARK WORLDWIDE, INC., Neenah, WI (US)

(72) Inventors: Andrew T. Baker, Norcross, GA (US); Elizabeth Deibler Gadsby, Mariette, GA (US); Russell F. Ross, Atlanta, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days. days.

(21) Appl. No.: 14/914,302

(22) PCT Filed: Apr. 29, 2015

(86) PCT No.: PCT/US2015/028154
§ 371 (c)(1),
(2) Date: Feb. 25, 2016

(87) PCT Pub. No.: WO2015/168214
PCT Pub. Date: Nov. 5, 2015

(65) Prior Publication Data
US 2017/0036005 A1    Feb. 9, 2017

Related U.S. Application Data

(60) Provisional application No. 61/996,148, filed on Apr. 30, 2014.

(51) Int. Cl.
*A61M 37/00* (2006.01)
*B29C 35/08* (2006.01)
(Continued)

(52) U.S. Cl.
CPC ..... *A61M 37/0015* (2013.01); *B29C 35/0805* (2013.01); *A61B 5/150022* (2013.01);
(Continued)

(58) Field of Classification Search
CPC ...... A61M 37/0015; A61M 2037/0023; A61M 2037/0053; A61M 2037/003;
(Continued)

(56) References Cited

U.S. PATENT DOCUMENTS 6,334,856 B1    1/2002    Allen et al.
6,558,361 B1    5/2003    Yeshurun
(Continued)

FOREIGN PATENT DOCUMENTS

CN    101912663 A    12/2010
WO    03059431 A1    7/2003
(Continued)

OTHER PUBLICATIONS

International Search Report of International Application No. PCT/US2015/028154, dated Aug. 3, 2015, 5 pages.
(Continued)

*Primary Examiner* — Bhisma Mehta
*Assistant Examiner* — Brandy S Lee
(74) *Attorney, Agent, or Firm* — Armstrong Teasdale LLP

(57) ABSTRACT

The configuration of an elongate aperture in a membrane draped over a microneedle assembly may be controlled by controlling the manner in which the aperture is formed and/or by controlling the manner in which the membrane is draped. At least a portion of the membrane may be spaced apart from a microneedle so that a gap is defined between the membrane and the microneedle. The gap may be configured for at least partially controlling the formation of the elongate aperture. The shape of the gap may optionally be at least partially defined by a pleat in the membrane. Any pleats may be aligned in a predetermined manner. The elongate aperture may be formed by a piercing member that is passed through a hole in the microneedle assembly prior to piercing the membrane. The piercing member may be a laser beam.

34 Claims, 7 Drawing Sheets

(51) Int. Cl.
*B29L 31/00* (2006.01)
*A61B 5/15* (2006.01)

(52) U.S. Cl.
CPC ... *A61B 5/150435* (2013.01); *A61B 5/150984* (2013.01); *A61M 2037/0038* (2013.01); *A61M 2037/0053* (2013.01); *B29L 2031/753* (2013.01)

(58) Field of Classification Search
CPC .. A61M 2037/0061; A61M 2037/0038; A61M 2037/0046; A61K 9/0021; A61B 5/150282; A61B 5/150984; A61B 5/150022; A61B 5/150435; B81B 2201/055; B81C 1/00111; B29C 35/0805; B29L 2031/753

See application file for complete search history.

(56) References Cited

U.S. PATENT DOCUMENTS

| | | | |
|---|---|---|---|
| 6,565,532 B1 * | 5/2003 | Yuzhakov | A45D 34/04 604/142 |
| 2002/0045907 A1 | 4/2002 | Sherman et al. | |
| 2003/0135201 A1 | 7/2003 | Gonnelli | |
| 2003/0225360 A1 * | 12/2003 | Eppstein | A61M 37/0015 604/19 |
| 2004/0164454 A1 * | 8/2004 | Gartstein | A61M 37/0015 264/293 |
| 2004/0186419 A1 | 9/2004 | Cho | |
| 2005/0079711 A1 * | 4/2005 | Busta | B01L 3/0255 438/689 |
| 2005/0228340 A1 | 10/2005 | Cleary et al. | |
| 2008/0108959 A1 | 5/2008 | Jung et al. | |
| 2009/0099502 A1 | 4/2009 | Tokumoto et al. | |
| 2011/0144591 A1 * | 6/2011 | Ross | A61M 37/0015 604/173 |
| 2011/0237925 A1 | 9/2011 | Yue et al. | |
| 2013/0165861 A1 * | 6/2013 | Ross | A61B 17/205 604/173 |
| 2015/0306363 A1 * | 10/2015 | Meyer | A61M 37/0015 604/173 |

FOREIGN PATENT DOCUMENTS

| | | |
|---|---|---|
| WO | 2011070457 A2 | 6/2011 |
| WO | 2011135532 A2 | 11/2011 |
| WO | 2013170171 A1 | 11/2013 |

OTHER PUBLICATIONS

Written Opinion of the International Searching Authority for International Application No. PCT/US2015/028154, dated Aug. 3, 2015, 8 pages.

International Preliminary Report on Patentability for International Application No. PCT/US15/28154, dated Apr. 22, 2016, 6 pages.

\* cited by examiner

DRAPED MICRONEEDLE ARRAY

CROSS-REFERENCE TO RELATED APPLICATION

This application claims the benefit of U.S. Provisional Patent Application No. 61/996,148, which was filed on Apr. 30, 2014.

INCORPORATION BY REFERENCE

Each of WO 2012/020332 to Ross, WO 2011/070457 to Ross, WO 2011/135532 to Ross, US 2011/0270221 to Ross, US 2013/0165861 to Ross, and U.S. Provisional Patent Application No. 61/996,148 to Baker et al. is incorporated herein by reference in its entirety.

FIELD OF THE DISCLOSURE

The present subject matter relates generally to microneedle arrays that may be used for delivering drug formulations to a patient through the skin.

BACKGROUND

Numerous apparatus have previously been developed for the transdermal delivery of drugs and other medicinal compounds utilizing microneedle arrays. Microneedles have the advantage of causing less pain to the patient as compared to larger conventional needles. In addition, conventional subcutaneous (often intra-muscular) delivery of drugs via a needle acts to deliver large amounts of a drug at one time, thereby often creating a spike in the bioavailability of the drug. For drugs with certain metabolic profiles this is not a significant problem. However, many drugs benefit from having a steady state concentration in the patient's blood stream; a well-known example of such a drug is insulin. Transdermal drug delivery apparatus including microneedle arrays are technically capable of slowly administering drugs at a constant rate over an extended period of time. Alternatively, transdermal drug delivery apparatus including microneedle arrays may administer drugs at variable rates. Thus, transdermal drug delivery apparatus including microneedle arrays offer several advantages relative to conventional subcutaneous drug delivery methods.

There is a desire for microneedle arrays or assemblies that provide a new balance of properties.

SUMMARY

An aspect of this disclosure relates to controlling the configurations of at least some of the apertures in a membrane that is draped over the microneedles of a microneedle assembly. For example, the configurations of the apertures may be controlled by controlling the manner in which the apertures are formed and/or by controlling the manner in which the membrane is draped.

One aspect of this disclosure is the provision of an apparatus including a membrane draped over at least some of the microneedles of a microneedle assembly, wherein the microneedles extend outwardly from a base surface of the assembly, a pathway is at least partially defined by a microneedle of the microneedle assembly, and the draped membrane includes an elongate aperture that is open along a length of the pathway so that the elongate aperture is in fluid communication with the pathway. The pathway may comprise a channel that is at least partially defined by the microneedle, wherein the length of the channel and the length of the elongate aperture extend in substantially the same direction.

In accordance with another aspect of this disclosure, an apparatus includes a membrane draped over at least some of the microneedles of a microneedle assembly, wherein the microneedles extend outwardly from a base surface of the assembly, a pathway is at least partially defined by a microneedle of the microneedle assembly, and at least a portion of the membrane may be spaced apart from the microneedle so that a gap is defined between the membrane and the microneedle. The gap may extend both at least partially around the microneedle and at least partially along the microneedle. The draped membrane may include an aperture that is in fluid communication with the pathway. The aperture may be elongate, so that the aperture is open along a length of the pathway.

The gap may be configured in a manner that at least partially controls the formation of the aperture in the membrane. As a more specific example, the shape and/or size of the gap may at least partially control the shape and/or size of the aperture in the membrane. In one example, the size of the gap and the size of the aperture in the membrane are inversely proportional to one another. As another example, the shape of the gap may be at least partially defined by one or more pleats in the membrane, although pleats are optional and may be omitted. If pleats are present, at least some of them may be aligned with one another in a pleat-alignment direction, and the pleat alignment direction may be parallel or non-parallel with a pathway-alignment direction in which at least some of the pathways of the microneedle assembly are aligned.

In accordance with one aspect of this disclosure, a method includes arranging a membrane and a microneedle assembly in an overlying relationship with one another so that the membrane is proximate at least a portion of a microneedle of the microneedle assembly, and forming an aperture in the membrane so that the aperture is in fluid communication with at least one hole of the microneedle assembly, wherein the forming of the aperture is comprised of both piercing the membrane with a piercing member while the membrane is proximate at least the portion of the microneedle, and introducing the piercing member into the at least one hole extending at least through the base. The introducing of the piercing member into the at least one hole may occur prior to the piercing of the membrane with the piercing member. More specifically, the piercing member may be passed through the at least one hole prior to the piercing of the membrane with the piercing member, wherein the piercing member may be introduced into the at least one hole through an opening to the at least one hole that is on the opposite side of the microneedle assembly from the membrane. The piercing member may be a laser beam.

In accordance with another aspect of this disclosure, a method includes arranging a membrane and a microneedle assembly in an overlying relationship with one another, wherein at least some of the pathways of the microneedle assembly are aligned with one another in a pathway-alignment direction, and the method further includes arranging the pathway-alignment direction and a direction of greatest elongation in the membrane in a predetermined configuration with respect to one another. The membrane may be mounted to the microneedle assembly while both the membrane and the microneedle assembly are in the overlying relationship with one another, and the pathway-alignment direction and the direction of greatest elongation in the membrane are in the predetermined configuration with respect to one another. The direction of greatest elongation in the membrane may be at least partially defined by tensioning the membrane in a direction that is substantially parallel to the direction of greatest elongation in the membrane. The arranging of the pathway-alignment direction and the direction of greatest elongation may be comprised of causing relative movement, such as relative rotation, between the membrane and the microneedle assembly. Pleats may be formed in the membrane and the pleats may extend in the direction of greatest elongation, although the pleats are optional and may be omitted.

The foregoing presents a simplified summary of some aspects of this disclosure in order to provide a basic understanding. The foregoing summary is not extensive and is not intended to identify key or critical elements of the invention or to delineate the scope of the invention. The purpose of the foregoing summary is to present some concepts of this disclosure in a simplified form as a prelude to the more detailed description that is presented later. For example, other aspects will become apparent from the following.

BRIEF DESCRIPTION OF THE DRAWINGS

In the following, reference is made to the accompanying drawings, which are not necessarily drawn to scale and may be schematic. The drawings are exemplary only, and should not be construed as limiting the invention.

DETAILED DESCRIPTION

Exemplary embodiments are described below and illustrated in the accompanying drawings, in which like numerals refer to like parts throughout the several views. The embodiments described provide examples and should not be interpreted as limiting the scope of the inventions. Other embodiments, and modifications and improvements of the described embodiments, will occur to those skilled in the art, and all such other embodiments, modifications, and improvements are within the scope of the present invention.

Figure 1:
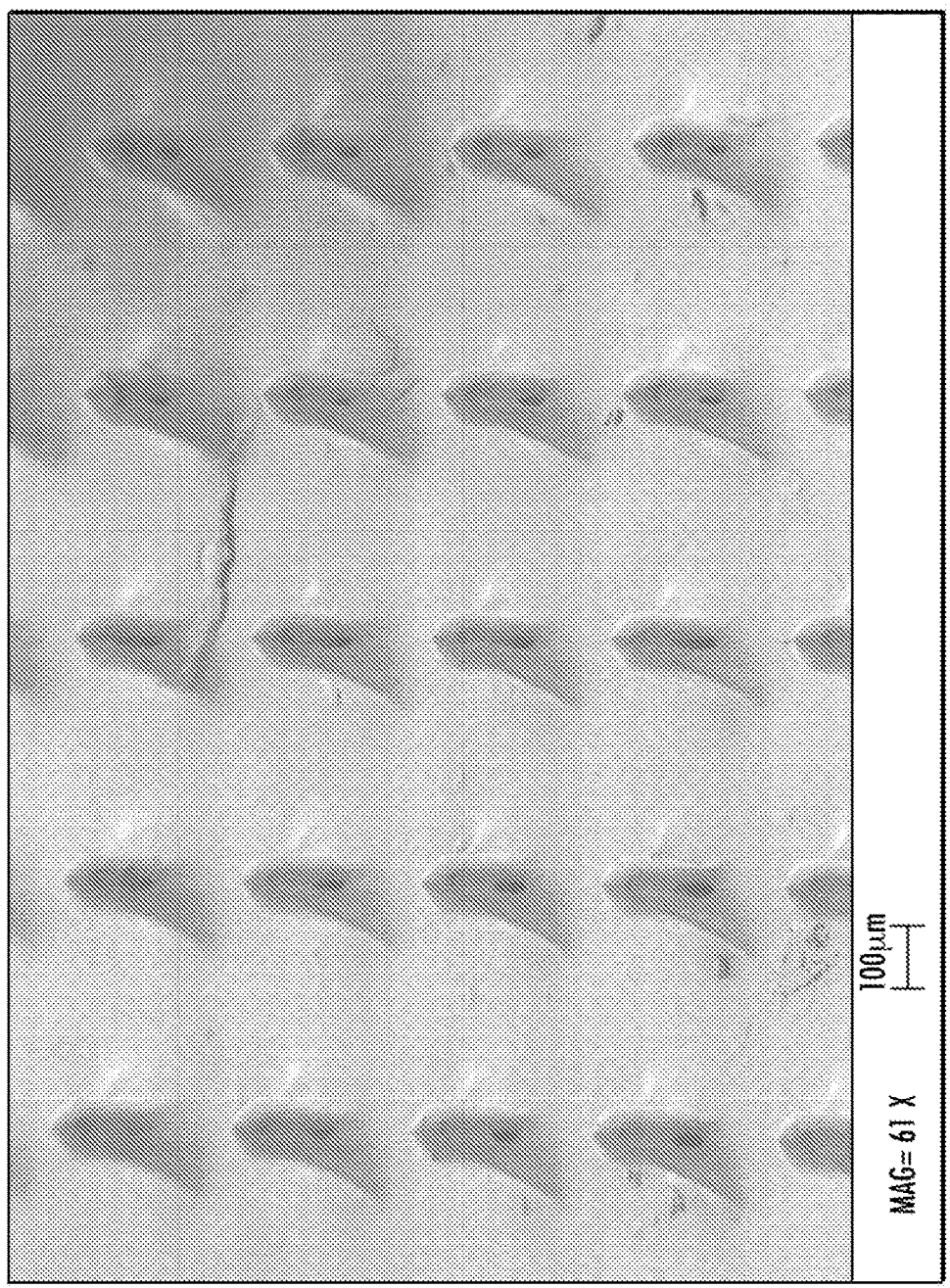
FIG. 1 is a bottom pictorial view (i.e., micrograph) of a portion of a membrane-draped microneedle assembly of a drug delivery apparatus, in accordance with a first embodiment of this disclosure.

FIG. 1 is a micrograph of a portion of a membrane-draped microneedle assembly that may be used as part of a drug delivery apparatus, in accordance with a first embodiment of this disclosure. As may be best understood by also referring to FIG. 2, at least some of the underlying shape of the microneedle assembly or array 12 is seen in FIG. 1, although the actual surface of the microneedle array is substantially hidden from view behind the nontransparent draped membrane 14 in FIG. 1. Alternatively, the draped membrane 14 may be more transparent. FIG. 1 further shows optional pleats (e.g., see pleats 16 in FIGS. 3, 9 and 10A) and apertures (e.g., see elongate apertures 18 in FIGS. 3 and 10A) in the draped membrane 14, as will be discussed in greater detail below. The pleats 16 are optional because in some versions of embodiments of this disclosure the pleats are omitted, as will be discussed in greater detail below.

Figure 2:
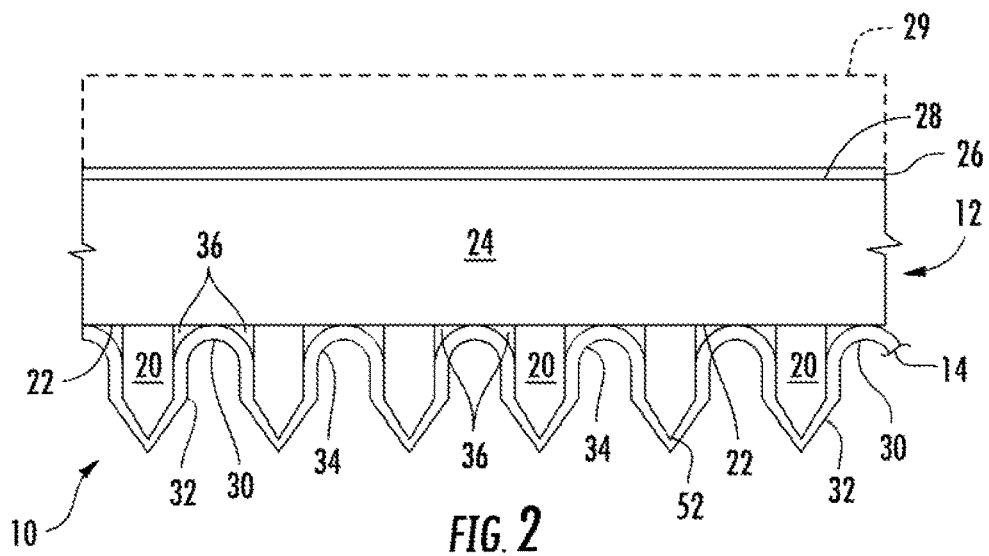
FIG. 2 is a schematic, enlarged, cross-sectional view of a portion of the drug delivery apparatus of the first embodiment, wherein included in FIG. 2 are portions of a microneedle assembly, a membrane draped across microneedles of the microneedle assembly, and a control membrane extending across the back surface of the microneedle assembly and partially defining a reservoir or plenum chamber.

FIG. 2 schematically illustrates a cross-section of at least a portion of a drug delivery apparatus 10 of the first embodiment, wherein the drug delivery apparatus includes the membrane-draped microneedle assembly of FIG. 1. That is, the apparatus 10 includes a microneedle array or assembly 12, and at least one membrane 14 draped at least partially across microneedles 20 and a front surface 22 (e.g., base surface) of the microneedle assembly. The front surface 22 may be referred to as a base or front surface of an assembly base 24 of the microneedle assembly 12. The microneedles 20 may extend from the front surface 22 of the assembly base 24. The apparatus 10 may further include at least one rate control membrane 26 or other suitable membrane(s) that extend across a back surface 28 of the assembly base 24. The back surface 28 and/or the rate control membrane 26 may partially define a reservoir or plenum chamber 29 for providing a fluid to the microneedle assembly 12, wherein the fluid is typically provided to the microneedle assembly 12 by way of the rate control membrane 26 and/or other suitable membrane(s). The apparatus 10 may further include other suitable features, such as disclosed in one or more of the documents previously incorporated herein by reference.

Figure 3:
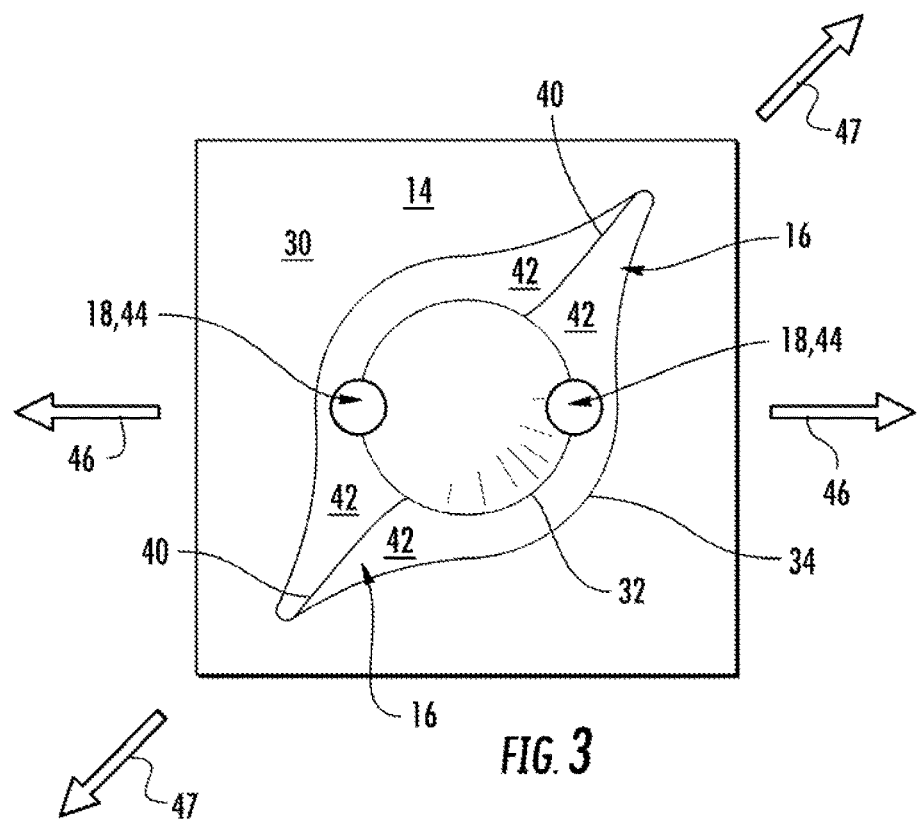
FIG. 3 is a schematic, enlarged, bottom plan view of a portion of the membrane-draped microneedle assembly of FIGS. 1 and 2, wherein a representative membrane-draped microneedle is shown.

The fluid supplied from the plenum chamber 29 may be in the form of a liquid drug formulation. Very generally described, the membrane-draped microneedles 20 are for penetrating a user's (e.g., patient's) skin, such as for providing the liquid drug formulation into the user's skin, such as by way of the elongate apertures 18 (FIGS. 3 and 10A). In accordance with one aspect of this disclosure, the positioning of the elongate apertures 18 and the pleats 16 (FIGS. 3, 9 and 10A) relative to one another, and/or the size of the pleats 16 may be chosen to at least partially control the size of the elongate apertures and, thus, the surface area of contact between the drug formulation and the skin, as will be discussed in greater detail below. However, the pleats 16 are optional and may be omitted, as will also be discussed in greater detail below.

FIG. 2 is schematic because, for example, the thicknesses of the draped and rate control membranes 14, 26 are exaggerated. The draped membrane 14 may comprise or be a polymeric (e.g., plastic) film, or the like, that may have been formed (e.g., extruded) separately from the microneedle assembly 12, and thereafter mounted to the microneedle assembly, as discussed in greater detail below. Optionally, the draped membrane may comprise or be an embossed or nano-imprinted, polymeric (e.g., plastic) film, or the like. For example, the draped membrane 14 may include nanotopography as disclosed by at least one of the documents previously incorporated herein by reference, although such features may be omitted. That is, any embossing or nanotopography of the draped membrane 14 may be omitted. As one example, the draped membrane 14 may comprise a polyether ether ketone (PEEK) film that is about five microns thick, or the draped membrane may be any other suitable material, such as a polypropylene film.

The rate control membrane 26 may be fabricated from permeable, semi-permeable or microporous materials known in the art for controlling the rate of flow of drug formulations, or the like. At least in theory, there may be embodiments in which the rate control membrane is omitted. As another example, the rate control membrane 26 may be in combination with and/or replaced by one or more other suitable membranes.

As alluded to above, the microneedles 20 may be described as extending in an outward direction from the front surface 22 of the assembly base 24. This outward direction from the assembly base 24, or the like, may serve as a frame of reference that may be used in the detailed description section of this disclosure for ease of understanding. For example and referring to FIG. 2, the draped membrane 14 may be characterized as including opposite inner and outer portions 30, 32, and intermediate portions 34 extending between respective inner and outer portions of the draped membrane. Whereas one or more frames of reference are established for use in this detailed description section of this disclosure for ease of understanding, the present invention may also be described and understood with reference to other suitable frames of reference, such that the present invention is not limited to the frames of reference used in this detailed description section of this disclosure.

Typically, at least immediately after the draped membrane 14 is mounted to the microneedle assembly 12, each of the inner portions 30 of the draped membrane may be proximate, facing toward or in opposing face-to-face relation with at least a portion of the front surface 22 of the assembly base 24. More specifically, each of, a majority of, or at least some of the inner portions 30 of the draped membrane 14 may optionally be in opposing face-to-face contact with at least a portion of the front surface 22 of the assembly base 24. Even more specifically, any face-to-face contact between an inner portion 30 and the front surface 22 may optionally extend substantially continuously around an adjacent microneedle 20, such as to define a substantially continuous annular contact area. Similarly, each, a majority of, or at least some of the outer portions 32 of the draped membrane 14 may be proximate or in opposing face-to-face contact with at least an outer portion of a respective microneedle 20. More specifically, each outer portion 32 may be in opposing face-to-face contact with an outer portion of the respective microneedle 20 substantially throughout a substantially continuous annular contact area. Wherever the draped membrane 14 is in opposing face-to-face contact with the microneedle assembly 12, the draped membrane may be adhered to the microneedle assembly, as will be discussed in greater detail below.

Each of, a majority of, or at least some of the intermediate portions 34 of the draped membrane 14 may be out of contact with and in opposing face-to-face relation with both an inner portion of a respective microneedle 20 and a portion of the front surface 22 of the assembly base 24, so that a gap 36 is defined between the intermediate portion 34 and the microneedle assembly 12. For each microneedle 20, the associated gap 36 may extend at least partially along the microneedle; and the gap may also extend at least partially around at least a portion of the microneedle, or the gap may extend substantially completely around at least an inner portion of the microneedle. In the first embodiment, it is typical for the gaps 36 to be annular and extend completely around the microneedles 20. In addition, the gaps 36 may taper along a length of the microneedles 20 so that the gaps becomes narrower toward the outer ends of the microneedles. In accordance with one aspect of this disclosure, the positioning of the elongate apertures 18 and the gaps 36 relative to one another, the size of the gaps, and/or the shape of the gaps may be chosen to at least partially control the size of the elongate apertures and, thus, the surface area of contact between the drug formulation and the skin, as will be discussed in greater detail below. Optionally, the pleats 16 may be included and/or controlled for adjusting the size and shape of the gaps 36, although the size and shape of the gaps 36 may be adjusted in any other suitable manner. That is, the pleats 16 may be optional features that can be omitted or substantially minimized.

As shown in FIG. 1 and identified with reference numerals for the representative draped microneedle in FIG. 3, the draped membrane 14 may optionally include folds that may be referred to as pleats 16. More specifically and referring to FIG. 3, the intermediate portions 34 of the draped membrane 14 may each include pairs of folds that may be referred to as a pair of pleats 16. When the pleats 16 are present, there may be at least a pair of pleats 16 positioned in substantially close proximity to (e.g., substantially engaging and extending outwardly from) at least some of, a majority of, or each of the microneedles 20. For each microneedle 20 and the associated pair of pleats 16, each pleat may be characterized as including at least one fold line 40 and opposite portions 42 of the draped membrane 14 that are joined to one another along the fold line. Each fold line 40 may extend arcuately along at least a portion of the length of the associated microneedle 20.

For each pleat 16, each of the opposite portions 42 of the draped membrane 14 that are part of the pleat 16 and are joined together by the fold line 40 of the pleat may be referred to as a pleat part 42. For each pleat 16 of the first embodiment, the pleat parts 42 of the pleat may be in opposing face-to-face relation with one another. For each pleat 16, except for being joined at the fold line 40, there may or may not be opposing face-to-face contact between the pleat parts 42 of the pleat. That is, for each of at least some of the pleats 16, there may be at least some opposing face-to-face contact between the pleat parts 42 of the pleat. As a contrasting example, for each of at least some of the pleats 16, the fold line 40 of the pleat may be referred to as defining or being part of a soft, rounded fold such that there may not be any substantially opposing face-to-face contact between the pleat parts 42 of the pleat. For each of at least some of the pleats 16, the pleat parts 42 of the pleat may extend divergently with respect to one another in a direction away from the fold line 40 of the pleat.

In FIG. 3, the elongate apertures 18 in the draped membrane 14 do not appear to be elongate since FIG. 3 is a plan view. In contrast, the elongate nature of the apertures 18 is apparent from FIGS. 1, 10A and 10B, wherein the apertures are shown extending along the lengths of the microneedles 20. The elongate apertures 18 may be shorter than shown FIG. 10A, and they may be positioned farther from the front surface 22 of the assembly base 24 than shown FIG. 10A, as will be discussed in greater detail below. Referring back to FIG. 3, each microneedle 20 of the first embodiment at least partially defines two pathways 44 (FIGS. 3 and 4) that enable the drug formulation to flow through the microneedle assembly 12 for being delivered into and/or through the user's skin. In the first embodiment, each elongate aperture 18 in the draped membrane 14 is substantially coextensive with, and substantially coaxial with, a portion of the respective pathway 44. That is, the pathways 44 and the elongate apertures 18 are cooperative for delivering the drug formulation from the plenum chamber 29 (FIG. 2) into and/or through the user's skin.

As schematically shown by what may be referred to as a pathway-alignment arrow 46 in FIG. 3, the pathways 44 of the microneedle 20 and the elongate apertures 18 of the draped membrane 14 are substantially aligned with one another in a pathway-alignment direction 46. Similarly, if the pleats are present and as schematically shown by what may be referred to as a pleat-alignment arrow 47 in FIG. 3, the pleats 16 and their fold lines 40 are substantially aligned with one another in the pleat-alignment direction 47. In the version of the first embodiment that includes pleats 16, substantially all of the pathways 44 and the elongate apertures 18 are substantially aligned with one another in the pathway-alignment direction 46, substantially all of the pleats 16 and their fold lines 40 are substantially aligned with one another in the pleat-alignment direction 47, and the pathway-alignment direction 46 and the pleat-alignment direction 47 are not parallel with one another. More specifically and as shown in FIG. 3, the pathway-alignment direction 46 and the pleat-alignment direction 47 extend obliquely to one another, as will be discussed in greater detail below. Reiterating from above, a microneedle 20 may have less than or more than two pathways 44 associated therewith, and it is not required that all of the pathways 44 and the elongate apertures 18 be aligned with one another in the pathway-alignment direction 46.

The pleats 16 may be referred to as major pleats 16, and the draped membrane 14 may further include other pleats, such as minor pleats (e.g., see FIG. 15) that may be relatively small as compared to the major pleats 16. The pleat-alignment direction of the minor pleats may extend crosswise to the pleat-alignment direction 47 of the major pleats. Accordingly, it may be generally stated that at least some of the pleats (e.g., at least some of the major pleats 16) of the draped membrane 14 may be aligned with one another in the pleat-alignment direction 47. Similarly, at least some of the pathways 44 and elongate apertures 18 may be aligned with one another in the pathway-alignment direction 46.

Figure 4:
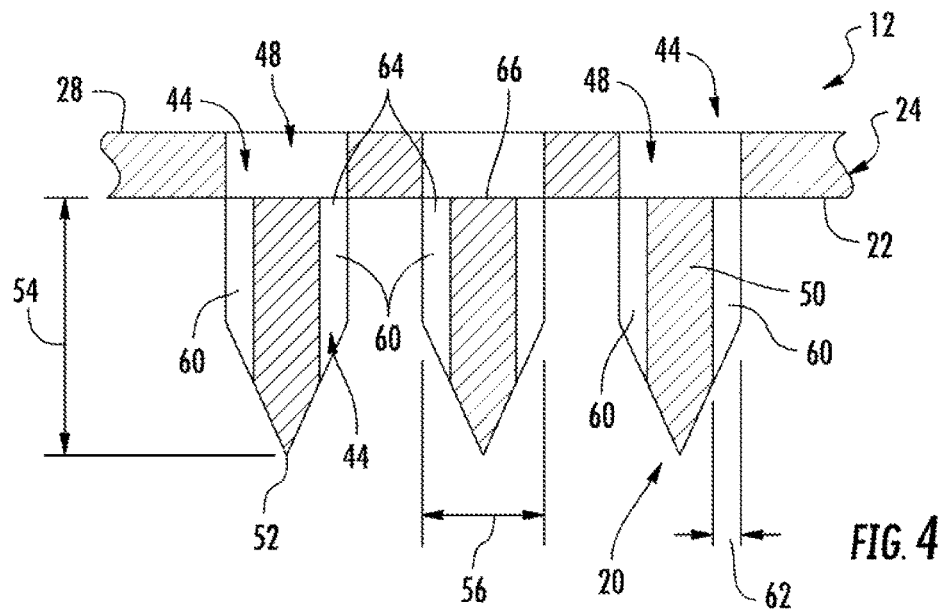
FIG. 4 is a schematic, isolated, enlarged, side cross-sectional view of a portion of the microneedle assembly of FIGS. 1 and 2, wherein the cross section is taken substantially along line 4-4 of FIG. 5.

Considering the microneedle assembly 12 in isolation as shown in FIG. 4, it may, for example, be configured at least generally as disclosed in one or more of the documents previously incorporated herein by reference. Generally, the microneedle assembly 12 is configured for delivering a fluidic drug formulation into and/or through the user's skin, such as by being configured to include one or more microneedles 20 extending outwardly from a suitable substrate or support, wherein this substrate or support may be in the form of a support plate, and it may be more generally referred to as the assembly base 24.

As shown in the cross-sectional view of FIG. 4 and reiterating from above, the assembly base 24 has opposite front and back surfaces 22, 28, and the multiple microneedles 20 extend outwardly from the front surface 22. The assembly base 24 and microneedles 20 may generally be constructed from a rigid, semi-rigid or flexible sheet of material, such as a metal material, a ceramic material, a polymer (e.g., plastic) material and/or any other suitable material. For example, the assembly base 24 and microneedles 20 may be formed from silicon by way of reactive-ion etching, or in any other suitable manner.

The assembly base 24 typically defines one or more holes 48 extending between, and open at each of, the front and back surfaces 22, 28 for permitting the drug formulation to flow therebetween. For example, a single hole 48 may be defined in the assembly base 24 at the location of each microneedle 20 to permit the drug formulation to be delivered from the back surface 28 to such microneedle 20. However, in other embodiments, the assembly base 24 may define any other suitable number of holes 48 positioned at and/or spaced apart from the location of each microneedle 20.

Each microneedle 20 may include a needle base 50 that extends outwardly from the front surface 22 (e.g., base surface) and transitions to a piercing or needle-like shape (e.g., a conical or pyramidal shape, or a cylindrical shape transitioning to a conical or pyramidal shape) having a tip 52 that is distant from the front surface 22. The tip 52 of each microneedle 20 is disposed furthest away from the assembly base 24 and may define the smallest dimension (e.g., diameter or cross-sectional width) of each microneedle 20. Additionally, each microneedle 20 may generally define any suitable overall length 54 from the front surface 22 to its tip 52 that is sufficient to allow the microneedles 20 to penetrate the stratum corneum and pass into the epidermis of a user. It may be desirable to limit the overall length 54 of the microneedles 20 such that they do not penetrate through the inner surface of the epidermis and into the dermis, which may advantageously help minimize pain for the patient receiving the drug formulation. For example, in one embodiment, each microneedle 20 may have an overall length 54 of less than about 1000 micrometers (um), such as less than about 800 um, or less than about 750 um, or less than about 500 um (e.g., an overall length 54 ranging from about 200 um to about 400 um), or any other subranges therebetween. The overall length 54 of the microneedles 20 may vary depending on the location at which the apparatus 10 is being used on a user. For example, the overall length 54 of the microneedles 20 for an apparatus to be used on a user's leg may differ substantially from the overall length 54 of the microneedles 20 for an apparatus to be used on a user's arm. Each microneedle 20 may generally define any suitable aspect ratio (i.e., the overall length 54 over a cross-sectional width dimension 56 of each microneedle 20). In certain embodiments, the aspect ratio may be greater than 2, such as greater than 3 or greater than 4. In instances in which the cross-sectional width dimension 56 (e.g., diameter) varies over the overall length 54 of each microneedle 20, the aspect ratio may be determined based on the average cross-sectional width dimension 56.

Each microneedle 20 may define one or more channels 60 in fluid communication with the holes 48 defined in the assembly base 24. In general, the channels 60 may be defined at any suitable location on and/or within each microneedle 20. For example, the channels 60 may be defined along an exterior surface of each microneedle 20. As a more specific example, each channel 60 may be an outwardly open flute defined by the exterior surface of, and extending along the overall length 54 of, a microneedle 20. As will be discussed in greater detail below, the channels 60 may generally be configured to at least partially form the pathway 44 that enables the drug formulation to flow from the back surface 28 of the assembly base 24, through the holes 48 and into the channels, at which point the drug formulation may be delivered into and/or through the user's skin by way of the apertures 18 (FIGS. 3 and 10A). The channels 60 may be configured to define any suitable cross-sectional shape. In the first embodiment, each channel 60 may define a semi-circular shape. In another embodiment, each channel 60 may define a non-circular shape, such as a "v" shape or any other suitable cross-sectional shape.

The dimensions of the channels 60 defined by the microneedles 20 may be specifically selected to induce a capillary flow of the drug formulation. As is generally understood, capillary flow occurs when the adhesive forces of a fluid to the walls of a channel 60 are greater than the cohesive forces between the liquid molecules. Specifically, the capillary pressure within a channel 60 is inversely proportional to the cross-sectional dimension of the channel and directly proportional to the surface energy of the subject fluid, multiplied by the cosine of the contact angle of the fluid at the interface defined between the fluid and the channel. Thus, to facilitate capillary flow of the drug formulation through the microneedle assembly 12, the cross-sectional width dimension 62 of the channel(s) (e.g., the diameter of the channel 60) may be selectively controlled, with smaller dimensions generally resulting in higher capillary pressures. For example, in several embodiments, the cross-sectional width dimension 62 of the channels 60 may be selected so that the cross-sectional area of each channel 60 ranges from about 1,000 square microns (um$^2$) to about 125,000 um$^2$, such as from about 1,250 um$^2$ to about 60,000 um$^2$, or from about 6,000 um$^2$ to about 20,000 um$^2$, or any other subranges therebetween.

The microneedle assembly 12 may generally include any suitable number of microneedles 20. For example, in one embodiment, the actual number of microneedles 20 included within the microneedle assembly 12 may range from about 10 microneedles per square centimeter (cm$^2$) to about 1,500 microneedles per cm$^2$, such as from about 50 microneedles per cm$^2$ to about 1250 microneedles per cm$^2$, or from about 100 microneedles per cm$^2$ to about 500 microneedles per cm$^2$, or any other subranges therebetween.

The microneedles 20 may generally be arranged on the assembly base 24 in a variety of different patterns, and such patterns may be designed for any particular use. For example, in one embodiment, the microneedles 20 may be spaced apart in a uniform manner, such as in a rectangular or square grid or in concentric circles. In such an embodiment, the spacing of the microneedles 20 may generally depend on numerous factors, including, but not limited to, the overall length 54 and width of the microneedles 20, as well as the amount and type of drug formulation that is intended to be delivered through the microneedles 20.

Figure 5:
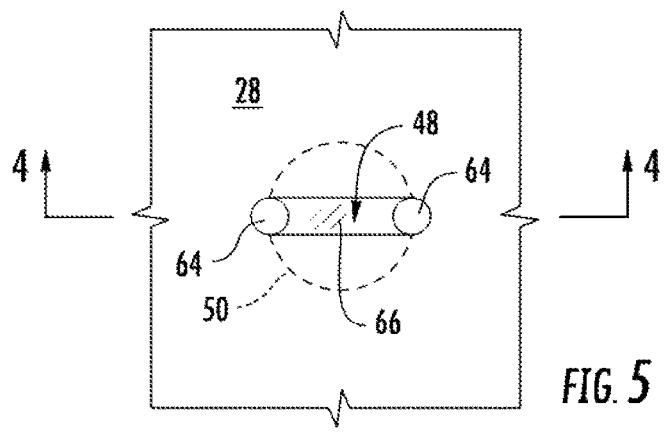
FIG. 5 is a schematic, enlarged, top plan view of a portion of the microneedle assembly of FIG. 4, wherein a portion of a representative microneedle that is hidden from view is shown in dashed lines.
Figure 6:
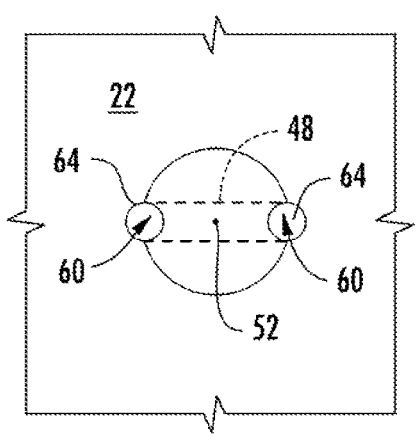
FIG. 6 is a schematic, enlarged, bottom plan view of the portion of the microneedle assembly of FIG. 5.

With continued reference to FIG. 4 and also referring to the top and bottom views of FIGS. 5 and 6, each channel 60 is in fluid communication with its associated hole 48 by way of an opening therebetween, wherein these openings may be referred to as junction openings 64. Referring to FIGS. 4 and 5, each hole 48 may be partially defined by an inner surface 66 positioned between a pair of the junction openings 64. FIG. 5 is schematic because the periphery of the needle base 50 is hidden from view and schematically illustrated by dashed lines. In contrast, FIG. 6 is schematic because a majority of the hole 48 is hidden from view and schematically illustrated by dashed lines.

The junction openings 64 may vary in area between pathways 44 on a given microneedle 20, and may vary between microneedles 20 on a given microneedle assembly 12. The area of each junction opening 64 may vary widely, and will depend on factors such as, for example, the diameter of the microneedle 20, the viscosity of the drug formulation to be moved through the pathways 44 and the quantity of the drug formulation to be delivered. The area of each junction opening 64 may also vary depending upon the desired size of the apertures 18 (FIGS. 3 and 10A) in the draped membrane 14, as will be discussed in greater detail below. For example, the area of each junction opening 64 at (e.g., in the plane of) the front surface 22 may be greater than or equal to about 100 square microns, although smaller areas may also be acceptable. In other examples, the area of the junction opening 64 at (e.g., in the plane of) the front surface 22 may be equal to about 150 square microns or greater. In the first embodiment, for each junction opening 64 and the adjacent channel 60, the junction opening and channel may be substantially concentric and may have substantially the same diameter, as will be discussed in greater detail below.

Figure 7:
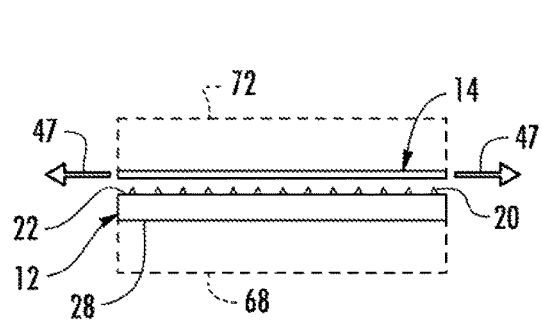
FIG. 7 schematically illustrates a system and method for draping a membrane over a microneedle assembly, in accordance with the first embodiment.

Examples of systems and methods for making the draped microneedle array 12 are discussed in the following, in accordance with the first exemplary embodiment. As schematically shown in FIG. 7, the draping process includes the draped membrane 14 and the microneedle assembly 12 being in an overlying configuration or overlying relationship with one another. More specifically, the draped membrane 14 is arranged for being draped over the front surface 22 of the microneedle assembly 12 in FIG. 7. In the overlying configuration shown in FIG. 7, the back surface 28 of the assembly base 24 may be supported by a vacuum box, downdraft system, or downdraft table 68, and/or in any other suitable manner. The draped membrane 14 may be at least partially supported by the tips 52 (FIGS. 2, 4 and 6) of the microneedles 20. The draped membrane 14 may also be at least partially supported by tensioning rollers, a tenter frame apparatus, and/or in any other suitable manner.

The pleat-alignment arrows 47 in FIG. 7 may be characterized as being schematically illustrative of tensioning rollers, a tenter frame, or the like. The tensioning rollers, tenter frame, or the like, may apply tension to the draped membrane 14 in a direction that is substantially the same as both the pleat-alignment direction 47 in the draped membrane and the direction of greatest elongation in the draped membrane 14. That is, when present, the pleats 16 typically form in the direction of greatest elongation in the draped membrane 14. Alternatively or in addition to the tensioning of the draped membrane 14 during the draping process, the direction of greatest elongation and the pleat-alignment direction 47 in the draped membrane 14 may be at least partially controlled by way of other factors, such as by the draped membrane being originally manufactured and/or previously processed in a manner that imparts a direction of least tensile strength, wherein the direction of least tensile strength may be substantially parallel to both the direction of greatest elongation and the pleat-alignment direction 47. Since the pleat-alignment direction 47 and the direction of greatest elongation in the draped membrane 14 may be substantially parallel to one another, the direction of greatest elongation may also be referred to by the numeral 47.

As shown in FIG. 7, the side of the draped membrane 14 that is opposite the microneedle assembly 12 may have pressure and/or heat applied thereto by way of a suitably equipped hood 72 or any other appropriate apparatus. Alternatively or in addition, heat may be applied more directly to the microneedle assembly 12. The magnitude and duration of the application of the vacuum, pressure and heating my be controlled to provide the above-discussed face-to-face contacts and so that portions of the draped membrane 14 are drawn at least partially into the open side channels 60 (FIGS. 4 and 6) at the outer portions of the microneedles 20. More specifically, the magnitude and duration of the application of the vacuum, pressure and heating my be controlled, and any angle (e.g., angle 76 in FIG. 8) between the pathway-alignment direction 46 (FIGS. 3 and 8) and the direction of greatest elongation 47 (FIGS. 3 and 8) may be controlled, so as to: provide the above-discussed contacts between the inner and outer portions 30, 32 of the draped membrane 14 and the respective portions of the microneedle assembly 12; provide and control the configuration of any gaps 36; and provide and control the configuration of any pleats 16. More generally, the operation of one or more of the tensioning rollers, tenter frame, or the like; downdraft table 68; and equipped hood 72 may be controlled for adjusting the size, shape and any orientation of the gaps 36 (FIG. 2), such as by causing the draped membrane 14 to include, or not include, the pleats 16.

The draped membrane 14 is typically fixedly mounted to the microneedle assembly 12 due to the resulting substantial conformity in shape between (e.g., the intimate contact between) the draped membrane and the microneedle assembly 12, and typically also as a result of the draped membrane becoming adhered to the microneedle assembly due to heating of the draped membrane. Any heating may be controlled (e.g., limited) so that it does not destroy any nanotopography on the surface of the draped membrane 14 that faces away from the microneedle assembly 12.

Figure 8:
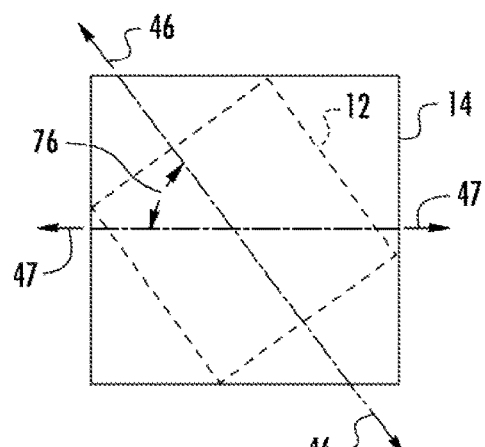
FIG. 8 is a schematic top plan view of the draped membrane and microneedle assembly of FIG. 7.

FIG. 8 is a schematic top plan view of the draped membrane 14 and microneedle assembly 12 as they may be arranged in FIG. 7. In FIG. 8, the microneedle assembly 12 is hidden from view beneath the draped membrane 14 and, therefore, the microneedle assembly is schematically illustrated by dashed lines. As shown in FIG. 8, the pathway-alignment direction 46 and the direction of greatest elongation 47 are not parallel with one another, and more specifically they extend obliquely to one another. In the first embodiment, the angle 76 defined between the pathway-alignment direction 46 and the direction of greatest elongation 47 is substantially the same as the corresponding angle defined between the pathway-alignment direction 46 and the pleat alignment direction 47 in FIG. 3. As shown in FIG. 8, the angle designated by the numeral 76 is the smaller of the two angles defined between the pathway-alignment direction 46 and the direction of greatest elongation 47. In the first embodiment, the angle 76 may be from about 20 degrees to about 80 degrees, or from about 30 degrees to about 70 degrees, or from about 40 degrees to about 60 degrees, or any other subranges therebetween. More specifically, the angle 76 is shown as being about 50 degrees in FIG. 8. There may also be other suitable angles between the pathway-alignment direction 46 and the other direction (e.g., direction of greatest elongation 47 and/or the pleat-alignment direction 47). For example, the angle 76 may be from about 10 degrees to about 170 degrees, or from about 20 degrees to about 160 degrees, or from about 30 degrees to about 150 degrees, or from about 40 degrees to about 140 degrees, or from about 50 degrees to about 130 degrees, or from about 60 degrees to about 120 degrees, or from about 70 degrees to about 110 degrees, or from about 80 degrees to about 100 degrees, or about 90 degrees, or any other subranges therebetween.

Figure 9:
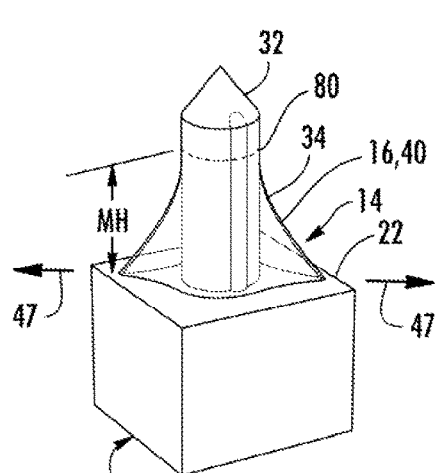
FIG. 9 is a schematic, enlarged, pictorial view a portion of the membrane-draped microneedle assembly prior to the forming of apertures in the draped membrane, wherein a representative membrane-draped microneedle is shown, in accordance with the first embodiment.
Figure 10A:
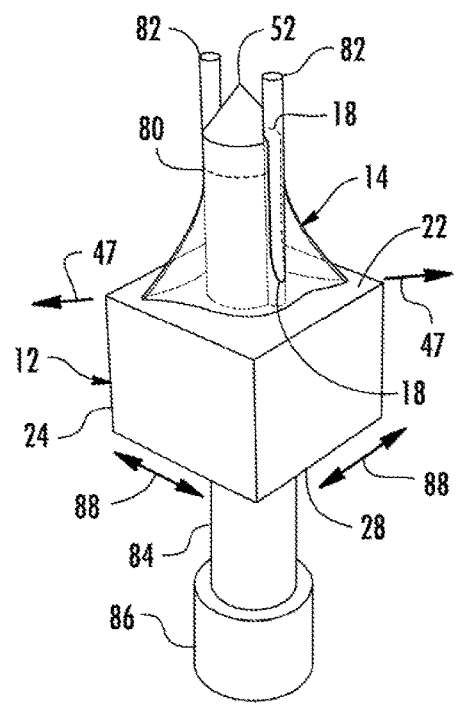
FIG. 10A is similar to FIG. 9, except for showing elongate apertures being formed by a laser, in accordance with the first embodiment.

FIG. 9 is a schematic, enlarged, pictorial view a portion of the membrane-draped microneedle assembly 12 after the draped membrane 14 has been mounted to the microneedle assembly but prior to the forming of the elongate apertures 18 (FIG. 10A) in the draped membrane. FIG. 9 is may be schematic because, for example, the draped membrane 14 is shown as being at least somewhat transparent, and an imaginary dimension line 80 has been included for showing the maximum height MH of both the gap 36 (FIG. 2) and the pleats 16 that may optionally be included for at least partially defining the shape and height of the gap. The maximum height MA of the gap 36 and pleats 16 is the shortest distance between the dimension line 80 and the base's front surface 22. In FIG. 9, the dimension line 80 indicates the height of the upper ends of the fold lines 40 of the pleats 16.

With an eye toward FIG. 9 (e.g., using the frame or reference of FIG. 9) and considering FIG. 2 upside down (i.e., so that the microneedles 20 point upwardly), in the version of the first embodiment that includes pleats 16, the following heights are substantially equal to one another and together vary around the perimeter of each microneedle 22 as a function of the angular position relative to the pleat-alignment direction 47 (e.g., relative to a vertical plane substantially containing the fold lines 40 of a pair of pleats): the height of the gap 36; the height of the upper edge of the draped membrane's intermediate portion 34, which is out of contact with the microneedle 20; and the height of the lower edge of the draped membrane's outer portion 32, which is in contact with the microneedle 20. These three heights may be collectively referred to as "the contact height." In the version of the first embodiment that includes pleats 16, the contact height varies gradually from a maximum contact height (e.g., maximum height MA) in a vertical plane intersecting the pleat-alignment direction 47, to a minimum contact height in a vertical plane that is perpendicular to the vertical plane intersecting the pleat-alignment direction 47. The minimum contact height may be less than about 75% of, less than about 50% of, less than about 30% of, or any other suitable percentage of, the maximum contact height. The size of the elongate apertures 18 (FIGS. 3 and 10A) may vary as a function of the contact height, as will be discussed in greater detail below. Alternatively, when the pleats 16 are omitted or substantially omitted, the following heights may remain about or substantially the same around the perimeter of each microneedle 22: the height of the gap 36; the height of the upper edge of the draped membrane's intermediate portion 34, which is out of contact with the microneedle 20; and the height of the lower edge of the draped membrane's outer portion 32, which is in contact with the microneedle 20.

As best understood with reference to FIG. 10A, the elongate apertures 18 may be formed by piercing the draped membrane 14 with one or more piercing members after the draped membrane 14 has been mounted to the microneedle array 12. In the first embodiment, the elongate apertures 18 are substantially directly aligned with the channels 60 (FIGS. 4 and 6) on the sides of the microneedles 20. A portion of the circumference of the elongate aperture 18 shown in FIG. 10A is schematically illustrated by a dashed line. The circumference of the elongate aperture 18 extends around an open area defined by the elongate aperture. This open area is for providing the area of contact between the drug formulation and the user's skin. In the first embodiment, the sum of the open areas defined by the elongate apertures 18 positioned within a square centimeter (in a plan view) of the draped microneedle assembly 12 may be at least 0.000005 cm$^2$, or at least about 0.000005 cm$^2$. That is, the elongate apertures 18 may be open along a sufficient length of the channels 60 so as to provided a total of least 0.000005 cm$^2$, or at least about 0.000005 cm$^2$, of open area per square centimeter of the draped microneedle assembly 12. This total open surface area is for providing the area of contact between the drug formulation and the user's skin. More specifically, the elongate apertures 18 may be open along a sufficient length of the channels 60 so as to provided a total of least 0.00007 cm$^2$, or at least about 0.00007 cm$^2$, of open area per square centimeter of the draped microneedle assembly 12. Even more specifically, the elongate apertures 18 may be open along a sufficient length of the channels 60 so as to provided a total of about 0.0002 cm$^2$ of open area per square centimeter of the draped microneedle assembly 12. For example, the elongate apertures 18 may be open along a sufficient length of the channels 60 so that the total amount of open area per square centimeter of the draped microneedle assembly 12 is within a range of about 0.000005 cm$^2$ to about 0.0001 cm$^2$, or more specifically within a range of about 0.00007 cm$^2$ to about 0.0002 cm$^2$, or any other subranges therebetween.

Figure 10B:
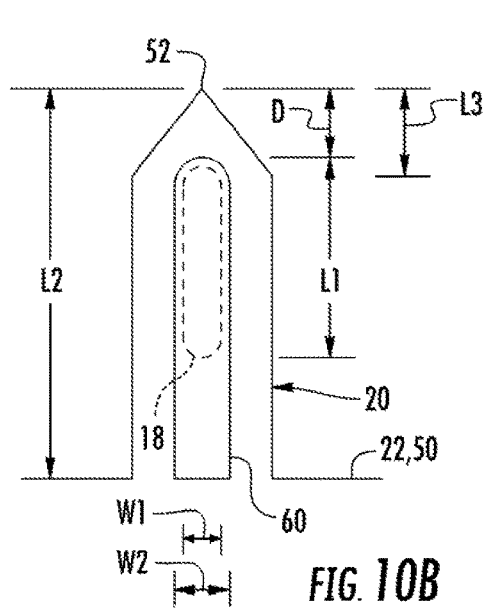
FIG. 10B is a schematic, isolated, side elevation view of a microneedle of the first embodiment, wherein an elongate aperture of the draped membrane is schematically shown superposed on a channel of the microneedle.

For the draped microneedles 20 of the first embodiment, the outer ends of elongate apertures 18 are typically positioned in substantially close proximity to the tips 52, and the opposite inner ends of elongate apertures 18 are spaced apart from the front surface 22 of the base 50. In contrast to the configurations of the elongate apertures 18 shown in FIGS. 1 and 10A, FIG. 10B shows that there may typically be a greater distance between the inner ends of elongate apertures 18 and the front surface 22 of the base 50. That is, for at least some of, a majority or, or each of the elongate apertures 18 and the respective microneedle 20, the elongate aperture 18 may be closer to the tip 52 of the microneedle than to the base 50. More specifically, an end of the elongate aperture 18 may be proximate or adjacent to the conical, pyramidal, or other suitably shaped portion of the tip 52.

For each of, a majority of, or at least some of the microneedles 20 and their associated elongate apertures 18 of the first embodiment, the relationship therebetween may be as shown in FIG. 10B and discussed in the following. In FIG. 10B, an elongate aperture 18 of the draped membrane 14 is schematically illustrated by dashed lines as being superposed on a channel 60 of a microneedle 20 of the microneedle assembly 12 (FIG. 4). In the side elevational view of FIG. 10B, the elongate aperture 18 has a length L1 and width W1, the microneedle 20 has an overall length L2 corresponding to the overall length 54 shown in FIG. 4 and discussed above, the channel 60 has a width W2, and an elevational distance D, or the like, is defined between an apex of the tip 52 of the microneedle 20 and the end of the elongate aperture 18 that is closest to the tip 52. The lengths L1, L2 and distance D extend in the same direction as one another, or more generally they extend in substantially the same direction as one another. The widths W1, W2 extend in the same direction as one another, or more generally they extend in substantially in the same direction as one another.

In the version of first embodiment shown in the drawings, the length L1 of the aperture 18 is greater than the width W1 of the aperture 18, so that the aperture 18 is elongate or elongated. As more specific examples the length L1 of the elongate aperture 18 may be at least about twice as large as the width W1 of the elongate aperture, or the length L1 of the elongate aperture may be at least about three, for or five times as large as the width W1 of the elongate aperture. Alternatively, the apparatus 10 may be configured such that the lengths L1 of the apertures 18 are smaller, for example so that the lengths L1 of the apertures may be about the same size as, or any other suitable ratio as compared to, the widths W1 of the apertures.

In the version of first embodiment shown in the drawings, the major axis of the elongate aperture 18 is parallel, or substantially parallel, to the major axis of the channel 60. The length L1 of the elongate aperture 18 may be within a range of at least 10% to no more than 80% of the overall length L2 of the microneedle 20, or any subranges therebetween. More generally, the length L1 of the elongate aperture 18 may be within a range of from about 10% to about 80% of the overall length L2 of the microneedle 20, or any subranges therebetween. More specifically, the length L1 of the elongate aperture 18 may be within a range of at least 20% to no more than 50% of the overall length L2 of the microneedle 20, the length L1 of the elongate aperture 18 may be within a range of from about 20% to about 50% of the overall length L2 of the microneedle 20, or any other subranges therebetween. Even more specifically, the length L1 of the elongate aperture 18 may about 30% of the overall length L2 of the microneedle 20.

The minor axis of the elongate aperture 18 may be perpendicular to, or substantially perpendicular to, the major axis of the channel 60. The width W1 of the elongate aperture 18 may be within a range of at least 70% to no more than 130% of the width W2 of the channel 60, or any subranges therebetween. More generally, the width W1 of the elongate aperture 18 may be within a range of about 70% to about 130% of the width W2 of the channel 60, or any subranges therebetween. More specifically, the width W1 of the elongate aperture 18 may be within a range of at least 90% to no more than 110% of the width W2 of the channel 60, the width W1 of the elongate aperture 18 may be within a range of about 90% to about 110% of the width W2 of the channel 60, or any other subranges therebetween.

The elevational distance D between the apex of the tip 52 of the microneedle 20 and the end of the elongate aperture 18 that is closest to the tip 52 may be no more than 30% of the overall length L2 of the microneedle 20, or any subranges therein. More generally, the elevational distance D between the apex of the tip 52 of the microneedle 20 and the end of the elongate aperture 18 that is closest to the tip 52 may be less than about 30% of the overall length L2 of the microneedle 20, or any subranges therein. More specifically, the elevational distance D between the apex of the tip 52 of the microneedle 20 and the end of the elongate aperture 18 that is closest to the tip 52 may be no more than 10% of the overall length L2 of the microneedle 20, or any subranges therein. The elevational distance D between the apex of the tip 52 of the microneedle 20 and the end of the elongate aperture 18 that is closest to the tip 52 may less than about 10% of the overall length L2 of the microneedle 20, or any subranges therein.

In one specific example, the length L1 of the elongate aperture 18 may be about 40% of the overall length L2 of the microneedle 20, the elevational distance D between the apex of the tip 52 of the microneedle 20 and the end of the elongate aperture 18 that is closest to the tip 52 may be about equal to the length L3 of the conical, or substantially conical, tip 52 of the microneedle 20, or any subranges therebetween.

The length L3 of the tip 52 may be about 20% of the overall length L2 of the microneedle 20. More specifically, the length L3 of the tip 52 may be about 60 um. More generally, the length L3 of the tip 52 may be within a range of about 10% to about 30% of the overall length L2 of the microneedle 20, or any subranges therebetween.

As schematically shown in FIG. 10A, the piercing members that form the elongate apertures 18 may be in the form of laser beams or laser beam portions 82. In FIG. 10A, the portion of the circumference of the elongate aperture 18 that is hidden from view behind the forwardmost laser beam portion 82 is schematically illustrated by a dashed line. The laser beam portions 82 may be portions of, or otherwise derived from, a relatively wide precursor laser beam 84 originating from a laser generator 86. The laser generator 86 may comprise a laser diode or any other suitable device for generating or otherwise providing the precursor beam 84. The laser generator 86 and the draped microneedle assembly 12 may be arranged so that the microneedle assembly 12 is positioned between the laser generator and the draped membrane 14, so that the precursor beam 84 is focused or otherwise directed toward and into the hole 48 (FIGS. 4 and 5) from the side of the assembly base 24 that is adjacent the back surface 28. The inner surface 66 (FIGS. 4 and 5) of the assembly base 24 and optionally also the back surface 28 of the assembly base may function as one or more obstructions or a mask for obstructing passage of a portion of the precursor beam 84. The obstructing of the passage of the precursor beam 84 may be characterized as splitting the precursor beam and, thus, providing at least the two beam portions 82.

The beam portions 82 shown in FIG. 10A are cylindrical and the pathways 44 (FIGS. 3 and 4) may be configured so that the elongate apertures 18 are formed in the draped membrane 14 substantially precisely at the location of the channels 60 (FIGS. 4 and 6). For example, any portions of the draped membrane 14 that are positioned in the channels 60 are typically exposed to the beam portions 82 and are, thus, removed (e.g., vaporized). As a more encompassing example, any portions of the draped membrane 14 that are positioned in the path of the beam portions 82 are typically removed, and the collimated beam portions shown in FIG. 10A are coaxial with, and have the same peripheral shape as, the junction openings 64 (FIGS. 5 and 6). Reiterating from above, the configuration of the junction openings 64 may vary, and for at least this reason the configurations of the beam portions 82 may vary such that the configurations of the apertures 18 may vary. The beams 82, 84 may be also varied in other ways, such as independently of the junction openings 64.

Depending upon various dimensions, the precursor beam 84 may simultaneously be directed into multiple holes 48 (FIGS. 4-6) and may be simultaneously split into a multiplicity of beam portions 82. Alternatively and/or in addition, and as schematically illustrated by arrows 88 in FIG. 10A, there may be relative movement between the laser generator 86 and the draped microneedle assembly 12 in various directions so that the precursor beam 84 may be serially directed into the holes 48. For example, the laser generator 86 may be mounted to the movable carriage of a computer-controlled gantry system, or the like, wherein the arrows 88 schematically illustrate the laser generator being moved by the gantry system or another suitable device.

Figure 11:
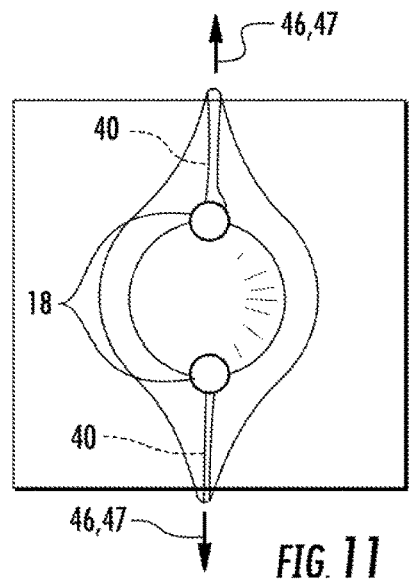
FIGS. 11-13 are respectively similar to FIGS. 3, 9 and 10A, except that FIGS. 11-13 illustrate a second embodiment of a draped microneedle assembly.
Figure 12:
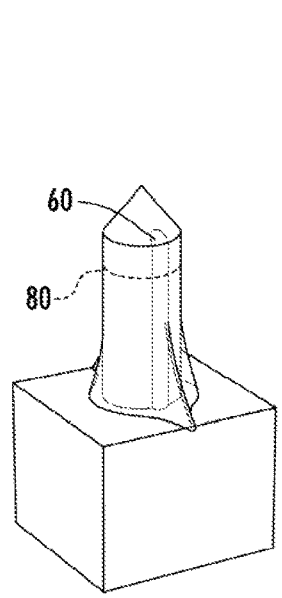
Figure 13:
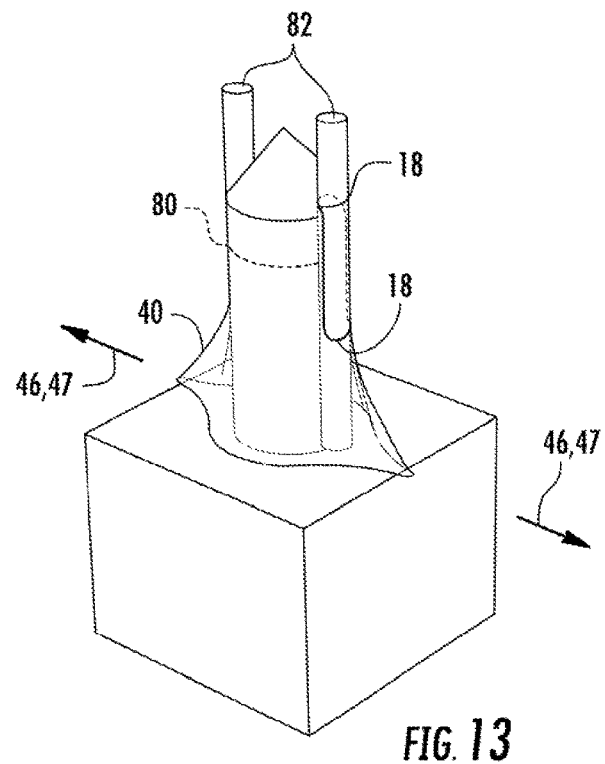

Second through fourth embodiments of this disclosure are like the first embodiment, except for variations noted and variations that will be apparent to those of ordinary skill in the art. For example and for the sake of providing a comparison, the first and second embodiments are identical except for differences in the angle 76 (FIG. 8) and differences caused by the differences in the angle 76. Referring to FIGS. 11-13, in the second embodiment the pathway-alignment and pleat-alignment directions 46, 47 and the direction of greatest elongation 47 all extend substantially in the same direction, so that the elongate apertures 18 of the second embodiment are shorter than the elongate apertures 18 of the first embodiment. More generally, the size of a gap 36 (FIG. 2) and the size of an associated aperture 18 in the draped membrane 14 can be inversely proportional to one another. When the pleat folds 40 align with the needle channels 60 as shown in FIGS. 11-13, the length of the (e.g., laser-formed) elongate apertures 18 may be more dependent upon the size (e.g., height) of the pleats 16, because the pleats may reduce the amount of the draped membrane 14 that extends into the channels 60. The height of the pleats 16 is schematically illustrated by the imaginary dimension line 80 in FIGS. 12 and 13.

In variations of both of the first and second embodiments, the junction openings 64 (FIGS. 4 and 5) may be configured so that only the portions of the draped membrane 14 that are positioned in the channels 60 are perforated (e.g., by the laser) to form the elongate apertures 18. In the variation of the first embodiment, the elongate apertures 18 may extend both above and below the height of the pleats 16 (e.g., dimension line 80 in FIGS. 9 and 10A). In contrast, in the variation of the second embodiment, the elongate apertures 18 may only extend above the height of the pleats 16 (e.g., dimension line 80 in FIGS. 12 and 13). Accordingly, when the pleat folds 40 do not align with the needle channels 60, the lengths of the (e.g., laser-formed) elongate apertures 18 are less dependent upon the height of the pleats 16.

Figure 14:
FIGS. 14 and 15 are similar to FIG. 1, except that FIGS. 14 and 15 respectively illustrate third and fourth embodiments of a draped microneedle assembly.

Referring to FIG. 14, the third embodiment may be like the variation to the first embodiment, except that the draping process of the third embodiment does not include the draped membrane 14 being drawn or otherwise forced into the channels 60. As a result, the apertures 18 in the draped membrane 14 of FIG. 14 are formed only at the ends of the channels 60, so that the apertures may not be elongate and are only located in close proximity to the tips 52.

Figure 15:
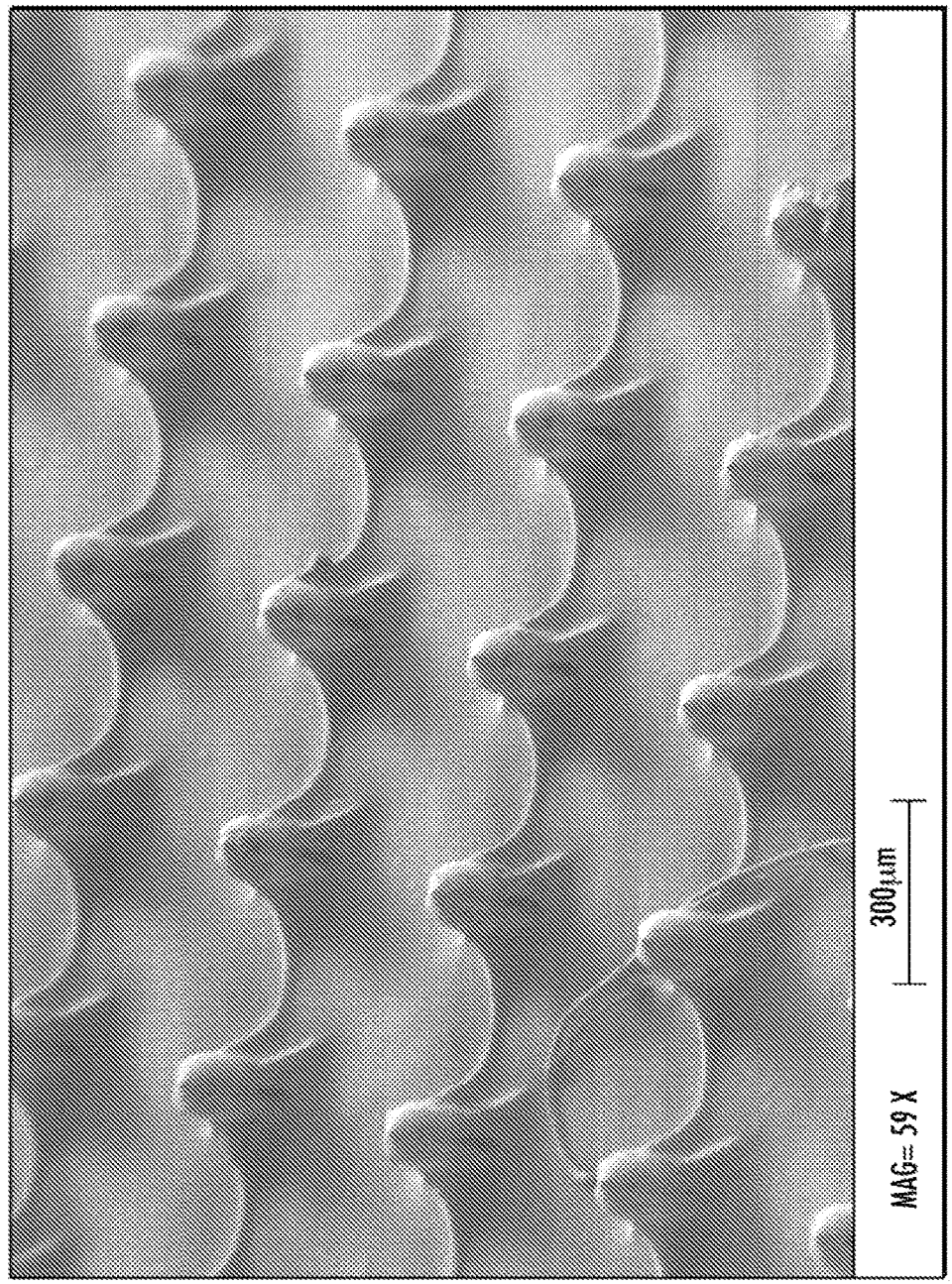

It is within the scope of this disclosure for one or more variables to be adjusted so that the apertures 18 and one or more other features may be configured differently. For example and as best understood with reference to FIG. 15, in the draped microneedle assembly 12 of the fourth embodiment, each channel 60 may be open to multiple apertures 18 in the draped membrane 14. That is, there may be separate apertures 18 respectively located at the top and proximate the bottom of each channel 60. As also shown in FIG. 15, the pleats 16 may include both relatively large pleats (e.g., major pleats) and relatively small pleats (e.g., minor pleats) extending crosswise to the relatively large pleats, and the relatively large pleats may optionally extend all the way between adjacent microneedles 20.

In accordance with one aspect of this disclosure, a draped microneedle array 12 may be configured and used in a manner that seeks to provide good delivery of the drug formulation through the user's skin by way of the microneedles 20 penetrating the outer barrier layers of the skin and causing the elongate apertures 18 and any optional nanotopography of the draped membrane 14 to come into good contact with living skin cells, so that the elongate apertures 18 provide good surface areas of contact between the drug formulation and the living skin cells, and any nanotopography of the draped membrane 14 (e.g., a nano-imprinted film) may enhance the permeability of the skin. In accordance with one aspect of this disclosure, the draped microneedle array 12 may simultaneously provide good contact between the skin and the film 14 while still providing good total surface area contact between the drug formulation fluid and the skin by way of the elongate apertures 18, wherein these results may be achieved, for example, by controlling the configurations of the gaps 36 (e.g., such as by controlling any pleated shape of the draped nano-imprinted film 14) and/or the laser perforating process, as discussed above.

For ease of understanding in this detailed description section of this disclosure, positional frames of reference, such as "top," "bottom," "front," "back," "over," "above," "below," and "height" have been used. However, the present invention is not limited to the positional frames of reference used in the detailed description section of this disclosure because, for example, the apparatus 10 of the exemplary embodiment may be configured so that it may be used in both inverted and uninverted configurations.

For ease of description in the foregoing, each microneedle 20 may have been described as having at least a pair of pleats 16 associated therewith; however, it is within the scope of the exemplary embodiments for the draped membrane 14 not to include pleats in close proximity to each and every one of the microneedles 20. Moreover, pleats 16 may be completely or substantially omitted. Similarly, references may have been made in the forgoing to each of one or more of other features; however, it is within the scope of the exemplary embodiments for there to be variations between one or more features of a plurality of features.

The above examples are in no way intended to limit the scope of the present invention. It will be understood by those skilled in the art that while the present disclosure has been discussed above with reference to exemplary embodiments, various additions, modifications and changes can be made thereto without departing from the spirit and scope of the invention, some aspects of which are set forth in the following claims.

What is claimed is:

1. An apparatus comprising:
    a microneedle assembly comprising
        a base surface,
        a plurality of microneedles extending outwardly from the base surface, and
        a pathway at least partially defined by a microneedle of the microneedle assembly; and
    a membrane draped over at least a portion of the plurality of microneedles, the membrane comprising:
        an elongate aperture that is open along a length of the pathway so that the elongate aperture is in fluid communication with the pathway, wherein said elongate aperture has a length and a width, the length being greater than the width,
        an outer portion in opposing face-to-face contact with at least an outer portion of the microneedle, and
        an inner portion facing toward at least a portion of the base surface,
        wherein the membrane defines a pleat extending between the inner and outer portions of the membrane.

2. The apparatus according to claim 1, wherein a length of the elongate aperture is at least about twice as large as a width of the elongate aperture.

3. The apparatus according to claim 1, wherein a length of the elongate aperture extends in a direction, a length of the pathway extends in a direction that is substantially the same as the direction in which the length of the elongate aperture extends.

4. The apparatus according to claim 1, wherein:
    the pathway comprises a channel at least partially defined by the microneedle;
    a length of the channel extends in a direction;
    a length of the elongate aperture extends in a direction that is substantially the same as the direction in which the length of the channel extends.

5. The apparatus according to claim 1, wherein:
    the base surface is a first surface of a base structure of the microneedle assembly;
    the base structure further comprises a second surface opposite from the first surface; and
    the apparatus further comprises a reservoir that is proximate the second surface and in fluid communication with the microneedle, wherein the reservoir is in fluid communication with the elongate aperture of the membrane by way of the pathway.

6. The apparatus according to claim 1, wherein:
    at least a portion of the membrane is spaced apart from the microneedle so that a gap is defined between the membrane and the microneedle; and
    the gap extends both at least partially around the microneedle and at least partially along the microneedle.

7. The apparatus according to claim 1, wherein a length of the elongate aperture is within a range of from about 10% to about 80% of an overall length of the microneedle.

8. The apparatus according to claim 1, wherein a width of the elongate aperture is within a range of about 70% to about 130% of a width of the channel.

9. The apparatus according to claim 1, wherein:
    the elongate aperture includes opposite first and second ends;
    the first end is positioned between the second end and an apex of a tip of the microneedle; and
    a distance between the first end and the apex of the tip is less than about 30% of an overall length of the microneedle.

10. The apparatus according to claim 1, wherein:
    the elongate aperture includes opposite first and second ends;
    the first end is positioned between the second end and an apex of a tip of the microneedle; and
    a distance between the first end and the apex is about equal to a length of the tip of the microneedle.

11. The apparatus according to claim 10, wherein the length of the tip of the microneedle is within a range of about 10% to about 30% of an overall length of the microneedle.

12. The apparatus according to claim 1, wherein:
    the pleat is positioned proximate the microneedle; and
    a fold line of the pleat is not aligned with at least one feature selected from the group consisting of the pathway and the elongate aperture.

13. An apparatus comprising:
    a microneedle assembly comprising
        a base surface,
        a plurality of microneedles extending outwardly from the base surface, and
        a pathway at least partially defined by a microneedle of the microneedle assembly; and
    a membrane draped over at least a portion of the plurality of microneedles, the membrane comprising an elongate aperture that is open along a length of the pathway so that the elongate aperture is in fluid communication with the pathway, wherein said elongate aperture has a length and a width, the length being greater than the width, and wherein the membrane defines a pleat positioned proximate the microneedle; and a fold line of the pleat is not aligned with at least one feature selected from the group consisting of the pathway and the elongate aperture.

14. The apparatus according to claim 13, wherein:

the pleat is positioned adjacent to the microneedle so that a gap is defined between the microneedle and at least a portion of the pleat that is opposing face-to-face relation with the microneedle;

the fold line of the pleat is not aligned with the pathway; and the fold line of the pleat is not aligned with the elongate aperture.

15. The apparatus according to claim 13, wherein the pleat comprises first and second portions of the membrane that are:

joined to one another along the fold line, and in opposing face-to-face relation with one another at a position distant from the fold line.

16. An apparatus comprising:

a microneedle assembly comprising a base surface, a plurality of microneedles extending outwardly from the base surface, and a pathway at least partially defined by a microneedle of the microneedle assembly; and a membrane draped over at least a portion of the plurality of microneedles, wherein the membrane comprises an aperture in fluid communication with the pathway, at least a portion of the membrane is spaced apart from the microneedle so that a gap is defined between the membrane and the microneedle, and the gap extends both at least partially around the microneedle and at least partially along the microneedle, wherein the gap is annular and extends completely around the microneedle, and wherein a size of the gap tapers along a length of the microneedle so that the gap becomes narrower toward a tip of the microneedle.

17. The apparatus according to claim 16, wherein the membrane covers a tip of the microneedle.

18. The apparatus according to claim 16, wherein the gap is in fluid communication with the pathway.

19. The apparatus according to claim 16, wherein the gap extends substantially completely around the microneedle.

20. The apparatus according to claim 16, wherein:

the membrane comprises an outer portion in opposing face-to-face contact with at least an outer portion of the microneedle, and an inner portion facing toward at least a portion of the base surface; and the gap is positioned between the inner and outer portions of the membrane.

21. A method, comprising:

arranging a membrane and a microneedle assembly in an overlying relationship with one another, wherein the microneedle assembly comprises a base having opposite first and second surfaces, a plurality of microneedles extending outwardly from the first surface, and a plurality of holes extending at least through the base, and the arranging of the membrane and the microneedle assembly in the overlying relationship with one another is comprised of the membrane being proximate at least a portion of a microneedle of the plurality of microneedles; wherein at least a portion of the membrane is spaced apart from the microneedle so that a gap is defined between the membrane and the microneedle, the gap being annular and extending completely around the microneedle;

forming an aperture in the membrane so that the aperture is in fluid communication with at least one hole of the plurality of holes, the forming being comprised of both piercing the membrane with a piercing member while the membrane is proximate at least the portion of the microneedle, and introducing the piercing member into the at least one hole extending at least through the base.

22. The method according to claim 21, wherein the introducing of the piercing member into the at least one hole occurs prior to the piercing of the membrane with the piercing member.

23. The method according to claim 21, comprising passing the piercing member through the at least one hole prior to the piercing of the membrane with the piercing member, wherein:

the passing of the piercing member through the at least one hole is comprised of the introducing of the piercing member into the at least one hole; and the introducing of the piercing member into the at least one hole is comprised of introducing the piercing member into the at least one hole by way of an opening to the at least one hole, wherein the opening to the at least one hole is defined by the second surface of the base.

24. The method according to claim 21, wherein the piercing member is a laser beam.

25. The method according to claim 24, wherein:

the aperture is a first aperture;

the method further comprises splitting the laser beam, the splitting being comprised of providing a first portion of the laser beam and a second portion of the laser beam;

the piercing of the membrane with laser beam is comprised of piercing the membrane with the first portion of the laser beam; and the method further comprises forming a second aperture in the membrane so that the second aperture is in fluid communication with the at least one hole, the forming of the second aperture being comprised of piercing the membrane with the second portion of the laser beam.

26. A method, comprising:

arranging a membrane and a microneedle assembly in an overlying relationship with one another, wherein the microneedle assembly comprises a plurality of microneedles extending outwardly from a base surface, and a plurality of pathways, and at least some of the pathways are aligned with one another in a pathway-alignment direction;

arranging the pathway-alignment direction and a direction of greatest elongation in the membrane in a predetermined configuration with respect to one another;

mounting the membrane to the microneedle assembly while both the membrane and the microneedle assembly in the overlying relationship with one another, and the pathway-alignment direction and the direction of greatest elongation in the membrane are in the predetermined configuration with respect to one another; and at least partially defining the direction of greatest elongation in the membrane, and tensioning the membrane in a direction that is substantially parallel to the direction of greatest elongation in the membrane.

27. The method according to claim 26, wherein the arranging of the pathway-alignment direction and the direction of greatest elongation is comprised of causing relative movement between the membrane and the microneedle assembly.

28. The method according to claim 26, wherein the arranging of the pathway-alignment direction and the direction of greatest elongation is comprised of causing relative rotation between the membrane and the microneedle assembly.

29. An apparatus comprising:
a microneedle assembly comprising
a base surface,
a plurality of microneedles extending outwardly from the base surface, and
a plurality of pathways at least partially defined by the plurality of microneedles; and
a membrane draped over the microneedle assembly, the membrane defining a plurality of pleats, wherein at least a portion of the membrane is spaced apart from the microneedle so that a gap is defined between the membrane and the microneedle, wherein the gap is annular and extends completely around the microneedle.

30. The apparatus according to claim 29, wherein:
at least some of the pleats being aligned with one another in a pleat-alignment direction in a plan view of the microneedle assembly draped with the membrane; and
at least some of the pathways being aligned with one another in a pathway-alignment direction in the plan view of the microneedle assembly draped with the membrane.

31. The apparatus according to claim 30, wherein the pathway-alignment and pleat-alignment directions are non-parallel with one another in the plan view of the microneedle assembly draped with the membrane.

32. The apparatus according to claim 30, wherein the pathway-alignment and pleat-alignment directions are substantially parallel with one another in the plan view of the microneedle assembly draped with the membrane.

33. The apparatus according to claim 30, wherein the pathway-alignment and pleat-alignment directions extend obliquely to one another in the plan view of the microneedle assembly draped with the membrane.

34. The apparatus according to claim 30, wherein:
the membrane further defines a plurality of apertures respectively in fluid communication with the plurality of pathways; and
at least some of the plurality of apertures are aligned with one another in the pathway-alignment direction in the plan view of the microneedle assembly draped with the membrane.

* * * * *